United States Patent [19]

Emodi et al.

[11] 4,029,805
[45] June 14, 1977

[54] SEMISYNTHETIC PENICILLINS

[75] Inventors: Alexander S. Emodi, West Orange; Harold Leon Newmark, Maplewood; Leonard Joseph Scialpi, Andover, all of N.J.

[73] Assignee: Hoffmann-La Roche Inc., Nutley, N.J.

[22] Filed: Feb. 13, 1976

[21] Appl. No.: 657,810

[52] U.S. Cl. .................. 424/271; 260/306.7 C
[51] Int. Cl.² .............. A61K 31/43; C07D 499/80
[58] Field of Search ............... 260/239.1, 306.7 C; 424/271

[56] References Cited
FOREIGN PATENTS OR APPLICATIONS 1,224,619  3/1971  United Kingdom ............ 260/239.1

Primary Examiner—Gerald A. Schwartz
Attorney, Agent, or Firm—Samuel L. Welt; Bernard S. Leon; Gerald S. Rosen

[57] ABSTRACT

Compounds represented by the formula

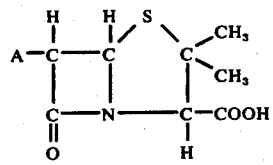

wherein A is

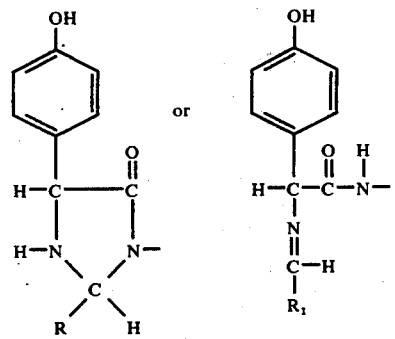

R is hydrogen, substituted or unsubstituted lower alkenyl or alkyl of 1 to 8 carbon atoms in the alkyl chain, phenyl or substituted phenyl, $R_1$ is phenyl, substituted phenyl or lower alkyl substituted with phenyl, hydrates thereof, and pharmaceutically acceptable basic salts of said compounds or hydrates, useful as antibacterial therapeutic agents in the treatment of infectious diseases caused by Gram-positive and Gram-negative bacteria, particularly Gram-negative bacteria and particularly advantageous because of their stability in aqueous solution are disclosed.

5 Claims, No Drawings

SEMISYNTHETIC PENICILLINS

Description of the Invention

This invention relates to antibacterial penicillin derivatives having enhanced stability in aqueous solution. More particuarly this invention relates to semisynthetic penicillins represented by the formula

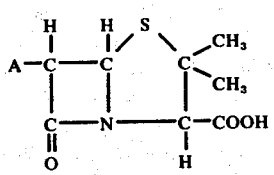

wherein A is

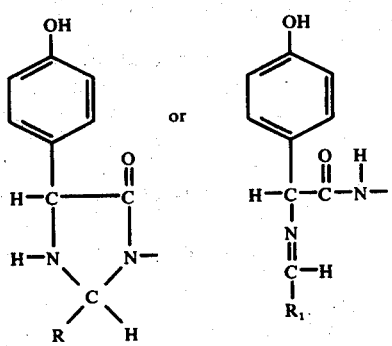

R is hydrogen, substituted or unsubstituted lower alkenyl or alkyl of 1 to 8 carbon atoms in the alkyl chain, phenyl or substituted phenyl, $R_1$ is phenyl, substituted phenyl or lower alkyl substituted with phenyl, and hydrates thereof,
and pharmaceutically acceptable base salts of said compounds of hydrates.

The pharmaceutically acceptable basic salts include salts with inorganic bases such as, for example, the alkali metal salts, e.g., sodium or potassium; ammonium salts, substituted ammonium salts, aluminium salts alkaline earth metal salts, e.g., calcium and the like; also salts with organic bases such as amines, e.g., trialkyl amines such as triethylamine; procaine, dibenzyl amine, N-benzyl-beta-phenethylamine, 1-ephenamine, N,N'-dibenzylethylene-diamine, dehydroabietylamine, N,N'-bis-dehydroabeitylethylene-diamine, arginine, N-methyal-glucamine and other amines which have been used to form salts with amoxicillin.

As used herein "lower alkenyl" means alkenyl groups with 2 to 8 carbon atoms, e.g., ethylene, propylene, butylene and the like. As used herein "lower alkyl" means straight or branched alkyl groups having from 1 to 8 carbon atoms, e.g., methyl, ethyl, propyl, ter.-butyl, iso-butyl, hexyl, pentyl, and the like. Substituents on the alkyl or alkenyl chains can be hydroxy, phenyl, substituted phenyl, halogen and the like, preferred is phenyl. "Substituted phenyl" includes hydroxy, halogen or lower alkyl substituted phenyls.

The compounds of this invention are produced by reacting an aldehyde of the formula R—CHO
or
$R_1$—CHO wherein R is hydrogen, substituted or unsubstituted lower alkenyl or lower alkyl of 1 to 8 carbon atoms in the alkyl chain, phenyl or substituted phenyl and $R_1$ is phenyl, substituted phenyl or lower alkyl substituted with phenyl,
with a semisynthetic penicillin of the formula

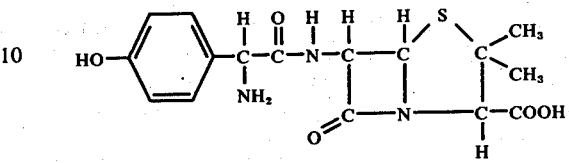

The reaction can be carried out in an aqueous basic medium to result in the corresponding base salt of the product. The resulting base salts are water soluble amorphous compounds which are relatively stable in aqueous solution as compared to the parent semisynthetic penicillins, especially in concentrated solutions, e.g., 10–20% w/v. In addition the compounds are significantly more stable in aqueous solution than the corresponding ketone reaction product.

The acid form of the compounds of this invention can be produced by conventional methods of converting carboxylic acid base salts to acids such as reacting the salt with hydrochloric acid. The free acids are amorphous compounds which are poorly water soluble.

Since the compounds of this invention contain an asymmetric carbon atom in the side chain, they can exist in two optically active isomeric forms. This invention includes both epimeric forms as well as the dl-mixture.

The compounds of this invention exhibit a profile of antibacterial activity similar to amoxicillin both in vitro and in vivo.

The compounds of this invention can be administered orally, parenterally, rectally or topically in suitable dosage forms and may be administered in the form of their salts.

The base salts of the compounds of this invention are relatively stable in solution and thus the compounds are particularly advantageous for use in situations where parenteral administration is indicated. The compounds are thus advantageous in this respect when compared to amoxicillin. Amoxicillin has very short stability in parenteral solutions which are usually prepared as salts with alkali metals, e.g., sodium or organic bases. In addition the compounds of this invention are more stable in aqueous solution than compounds prepared by the reaction of analogous ketones with amoxicillin.

For purposes of administration, the compounds of this invention can be combined with conventional compatible organic or inorganic pharmaceutical carrier materials known in the art. Such materials include, for example, water, gelatin, gums, lactose, starches, magnesium stearate, talc, vegetable oils, polyalkylene glycols, petroleum jelly and the like. Such pharmaceutical preparations may be in unit dosage form or solution and may additionally contain other therapeutically valuable substances or conventional pharmaceutical adjuvants such as preservatives, stabilizing agents, wetting agent, emulsifying agents, buffers and the like. The pharmaceutical preparations can be in conventional solid dosage forms such as tablets, capsules, dragees and the like, conventional semi-solid forms such as ointments, and creams, conventional dosage forms as suppositories, dry ampules and the like.

Dosage forms for parenteral use are formed by dissolving a powder of the base salt of the active compound with suitable sterile aqueous solvent prior to use. In the case of the relatively stable compounds of this invention, the solution can be formed many hours prior to use rather than immediately prior to use.

Typical suitable aqueous solvents include water for injection USP, suitable intravenous solutions include sodium chloride injection (saline) USP, dextrose injection, e.g., 5% or 10% USP and the like. Preservatives can be in the injection solutions.

The amount of active compound to utilize in treating bacterial infections varies with the needs of the patient in the judgement of the clinician. Generally, however, a sufficient amount of the acid or equivalent amount of salt is administered to parallel the dosage regimen of amoxicillin, i.e., the normal adult usually is administered from 250 mg. to 500 mg. about 3 or 4 times a day.

For injection, about 200 mg. to 500 mg. in 1 to 2 ml. are injected 3 to 4 times a day.

Typical solid oral dosage units contain 250 mg. to 500 mg., e.g., capsules. For parenteral use the following concentrations are suitable 100 mg./ml. to 250 ml.

It is understood that all dosage amounts are expressed in equivalent amounts of acid.

Because of the advantageous solubility characteristics of the basic salts of the active compounds of this invention, their absorption and diffusion characteristics are often superior to amoxicillin. Therefore, in some cases comparable molecular amounts of the active compounds are less toxic than the amoxicillin parent compound.

As used herein "amoxicillin" is 6[(−)-alpha-amino-para-hydroxyphenylacetamido]-penicillanic acid.

To illustrate the relative stability of the compounds of this invention in aqueous solution at room temperature the sodium salts of the compounds were tested as 20% by weight aqueous solutions for activity by microbiological assay using *B. subtilis* as the test organism and compared to 10% and 20% aqueous solutions of amoxicillin sodium salt and 10% aqueous solution of the acetone derivative of amoxicillin. It was done this way because more dilute solutions are more stable. The results are shown in the following Table.

The compounds are prepared by reacting on an approximately equimolar basis, an aqueous suspension of amoxicillin with the appropriate aldehyde and a 20% aqueous solution of an alkali metal hydroxide, preferably sodium hydroxide. The resulting product is then dried, e.g., freeze dried, spray dried. When being reconstituted, into an aqeous solution, the solution was a pH of about 7.2 to 8.0.

The resulting product is either an imidazolidinyl compound or a Schiff base, or a mixture thereof, depending on the aldehyde. Thus the lower alkyl aldehydes form predominately the imidazolidinyl derivative with little or no Schiff base. The phenyl substituted aldehydes on the other hand form, e.g., in the case of benzaldehyde, about 75% imidazolidinyl and 25% Schiff base derivative, while salicylaldehyde forms essentially the Schiff base. The derivative from, for example, p-fluoro-benzaldehyde has not yet been characterized as to structure but is probably predominantly the Schiff base.

The base salts formed as a result of the reaction of the aldehyde and amoxicillin in basic media are water soluble. These salts can be converted into the corresponding carboxylic acid as indicated above. The resulting acids are water-insoluble. Both the salts and acids as well as the hydrates thereof are amorphous materials.

The following examples illustrate the invention.

EXAMPLE 1

1 ml. of acetaldehyde and 2.5 ml. of a 20% w/w aqueous solution of NaOH (the latter added dropwise) were added to a stirred suspension of 6.5 g. amoxicillin trihydrate in 300 ml. $H_2O$. The resulting clear solution, after filtration through a 0.45 $\mu$ Millipore filter was frozen at −60° C. and freeze dried.

The product in aqueous solution has a pH of 7.4. The product has a molecular weight of 431.44 and a calculated empirical formula of $C_{18}H_{20}N_3O_5S$ $Na.H_2O$, and a melting point of 220° C. It is an amorphous, slightly yellow imidazolidinyl compound.

The free acid was formed by adding 4.2 ml. of 3N HCl to the product in aqueous solution rather than freezing it as above. The heavy precipitate which formed was collected on a 5 Millipore filter, washed with distilled water and vacuum dried. The resulting

TABLE I

| Amoxicillin Derivative From | % Concentration | % Retention (hours) | | | | | |
|---|---|---|---|---|---|---|---|
| | | 1 | 2 | 4 | 6 | 6½ | 24 |
| Acetaldehyde | 20 | 100 | 99 | 99 | 98 | 98 | 94 |
| Propionaldehyde | 20 | 95 | 90 | — | 78 | — | 72 |
| Butyraldehyde | 20 | 95 | 83 | — | 83 | — | 70 |
| Hexaldehyde | 20 | 100 | 100 | — | 94 | — | 90 |
| Caprylaldehyde | 20 | 93 | 96 | — | 96 | — | 93 |
| Benzaldehyde | 20 | 100 | 96 | — | 100 | — | 93 |
| 2-Phenylpropionaldehyde | 20 | 94 | 94 | — | 92 | — | 91 |
| Isobutyraldehyde | 20 | 100 | 100 | — | 97 | — | 82 |
| Acetone | 10 | 100 | 93 | 87 | 80 | 79 | 30 |
| Amoxicillin sodium salt | 10 | 100 | 91 | 65 | 59 | 58 | 38 |

The assays were performed by microbiological assay using the method described in 21 C.F.R. 436.105, revised Apr. 1, 1975.

The antibacterial activity retained in a 24 hour period by the acetaldehyde derivative when dissolved in 5% dextrose solutions at 0.5 and 1.0% concentration is 83% and 80% respectively. The sodium salt of amoxicillin retains less than 40% activity under the same conditions.

product is an amorphous powder. The product has an elemental analysis as follows:

Calc.: C 52.80, H 5.66, N 10.26; Found: C 53.50, H 5.75, N 9.50.

EXAMPLE 2

In order to illustrate the relative activity of the compounds of this invention as compared to amoxicillin, the compounds, represented by the acetaldehyde derivative, were tested orally against systemic bacterial infections of mice with the following results. The $CD_{50}$ is the curative dose in 50% of the animals treated against a challenge organism.

Table 2

| Organism | $CD_{50}$ in mg/kg PO | |
|---|---|---|
| | amoxicillin | acetaldehyde derivative of amoxicillin |

EXAMPLE 3

The active compounds of this invention were tested to determine acute toxicity and in vivo activity parenterally against representative systemic Gram positive and Gram negative bacteria and the results compared to amoxicllin in the same tests. The results are shown in the following Table.

Table 3

| (a) Acute Toxicity | $LD_{50}$ in mg/kg | | |
|---|---|---|---|
| Amoxicillin Derivative | SC | PO | IP |
| Acetaldehyde | >10,000 | >10,000 | 9,201 (8,886–10,000) |
| Butyraldehyde | 10,000 | >10,000 | 7,268 (7,070–7955) |
| Propionaldehyde | 7,955 | >10,000 | 10,000 (7,070–>10,000) |
| Amoxicillin | 10,000 (8,644–>10,000) | >10,000 | 3,463 (3,140–3,978) |

> X more than
< = less than
SC = subcutaneously
PO = per os
IP = intraperitoneally (b) Chemotherapeutic Activity

| | $CD_{50}$ : mg/kg | | | |
|---|---|---|---|---|
| | sc | | po | |
| Organism | Amoxicillin | Acetaldehyde Derivative | Amoxicillin | Acetaldehyde Derivative |
| S. aureus | 2.0 | 1.3 | 1.2 | 0.77 |
| S. pyogenes | <0.05 | <0.05 | 1.5 | 1.7 |
| D. pneumoniae | 0.53 | 0.76 | 10 | 12 |
| E. coli | 10 | 6.9 | 6.4 | 4.6 |
| K. pneumoniae | 12 | 11 | 10 | 17 |
| S. typhosa | 6.3 | 6.5 | 5.0 | 8.8 |
| S. schottmuelleri | 6.5 | 3.4 | 5.3 | 6.4 |

| | $CD_{50}$ : mg/kg | | | |
|---|---|---|---|---|
| | sc | | po | |
| Organism | Amoxicillin | Butyraldehyde Derivative | Amoxicillin | Butyraldehyde Derivative |
| S. aureus | 0.50 | 0.11 | 0.29 | 0.20 |
| S. pyogenes | <0.01 | 0.01 | 0.08 | <0.05 |
| D. pneumoniae | 3.2 | 2.5 | 2.7 | 2.1 |
| E. coli | 6.0 | 3.9 | 15 | 12 |
| K. pneumoniae | 22 | 16 | 58 | 46 |
| S. typhosa | 1.3 | 0.85 | 3.3 | 2.9 |
| S. schottmuelleri | 2.3 | 3.2 | 5.9 | 5.7 |

| | Amoxicillin | Propionaldehyde Derivative | Amoxicillin | Propionaldehyde Derivative |
|---|---|---|---|---|
| S. aureus | 0.47 | 0.13 | 0.41 | 0.54 |
| S. pyogenes | 0.07 | 0.08 | 0.16 | 0.12 |
| D. pneumoniae | 0.19 | 0.23 | 1.1 | 0.58 |
| E. coli | 3.4 | 4.4 | 11 | 11 |
| K. pneumoniae | 17 | 7.4 | 16 | 12 |
| S. typhosa | 2.8 | 3.5 | 3.8 | 3.9 |
| S. schottmuelleri | 6.1 | 1.9 | 5.7 | 5.0 |

| S. aureus | 1.2 | 0.77 |
|---|---|---|
| S. pyogenes | 1.5 | 1.7 |
| D. pneumoniae | 10 | 12 |
| E. coli | 6.4 | 5 |
| K. pneumoniae | 10 | 17 |
| S. typhosa | 5.4 | 8.8 |
| S. schottmuelleai | 5.3 | 6.4 |

| | $CD_{50}$ : mg/kg | | | |
|---|---|---|---|---|
| | sc | | po | |
| Organism | Amoxicillin | Hexaldehyde Derivative | Amoxicillin | Hexaldehyde Derivative |
| S. aureus | 0.79 | 0.68 | 0.72 | 1.7 |
| S. pyogenes | 0.11 | 0.56 | 0.30 | 0.61 |
| D. pneumoniae | 0.07 | 0.20 | 0.75 | 0.54 |
| E. coli | 2.5 | 5.8 | 10 | 17 |
| K. pneumoniae | 48 | 77 | 59 | 36 |

|                  |            |                       |            |                       |
|------------------|------------|-----------------------|------------|-----------------------|
| S. typhosa       | 3.3        | 4.7                   | 3.7        | 6.4                   |
| S. schottmuelleri| 1.0        | 1.7                   | 4.4        | 6.1                   |
|                  | Amoxicillin| Benzaldehyde Derivative| Amoxicillin| Benzaldehyde Derivative|
| S. aureus        | 0.16       | 1.6                   | 4.0        | 0.87                  |
| S. pyogenes      | 0.31       | 0.36                  | 0.82       | 0.28                  |
| D. pneumoniae    | 0.14       | 0.13                  | <0.20      | 0.32                  |
| E. coli          | 5.9        | 3.6                   | 16         | 8.0                   |
| K. pneumoniae    | 100        | 136                   | 75         | 50                    |
| S. typhosa       | 0.56       | 2.2                   | 1.3        | 2.8                   |
| S. schottmuelleri| 6.7        | 4.1                   | 5.5        | 9.4                   |

EXAMPLE 4

2.5 ml. of 20% w/w aqueous solution of NaOH are added dropwise to 1.2 ml. of propionaldehyde and the mixture is added to a stirred suspension of 6.5 g. amoxicillin trihydrate in 100 ml. $H_2O$. The resulting clear solution, after filtration through a 0.45 μ Millipore filter is frozen at −60° C. and freeze dried.

The product has a pH of about 7.9 in aqueous solution. The product has a molecular weight of 454.47 and a calculated empirical formula of $C_{19}H_{29}N_3NaO_5S.1.5H_2O$. The melting point is 220° C. It is an amorphous slightly yellow imidazolidinyl compound.

EXAMPLE 5

2.5 ml. of 20% w/w aqueous solution of a NaOH are added dropwise to 1.1 g. of butyraldehyde and the mixture is added to a stirred suspension of 6.5 g. amoxicillin trihydrate in 100 ml. $H_2O$. The resulting solution, after filtration through a 0.45 μMillipore filter is frozen at −60° C. and freeze dried.

The product has a pH of about 8.0 in aqueous solution. The product has a molecular weight of 476.48 and a calculated empirical formula of $C_{20}H_{24}N_3NaO_5S.2H_2O$ and a melting point of 220° C. It is amorphous slightly yellow imidazolidinyl compound.

EXAMPLE 6

2.5 ml. of 20% w/w aqueous solution of NaOH are added dropwise to 2.06 ml. of hexaldehyde and the mixture is added to a stirred suspension of 6.5 g. amoxicillin trihydrate in 100 ml. of $H_2O$. The resulting solution, after filtration through a 0.45 μMillipore filter is frozen at −60° C. and freeze dried.

The product (an amorphous slightly yellow imidazolidinyl compound) has a pH of about 8 in aqueous solution. The product has a molecular weight of 496.54 and a calculated empirical formula of $C_{22}H_{31}N_3NaO_5S.1.5H_2O$ and a melting point of 210° C.

EXAMPLE 7

2.5 ml. of 20% w/w aqueous solution of NaOH are added dropwise to 1.8 ml. of benzaldehyde and the mixture is added to a stirred suspension of 6.5 g. amoxicillin trihydrate in 100 ml. $H_2O$. The resulting solution afterfiltration through a 0.45 μMillipore filter is frozen at −60° C. and freeze dried.

The product (an amorphous, slightly yellow material) is a mixture of about 75% by weight imidazolidinyl compound and about 25% Schiff's base which has a pH of about 7.6 in aqueous solution. The product has an average molecular weight of 511.50 and the product has a melting point of 215° C.

EXAMPLE 8

2.5 ml. of 20% w/w aqueous solution of NaOH are added dropwise to 2.3 ml. of 2-phenylpropionaldehyde and the mixture is added to a stirred suspension of 6.5 g. amoxicillin trihydrate in 100 ml. $H_2O$. The resulting solution after filtration through a 0.45 μMillipore filter is frozen at −60° C. and freeze dried.

The product (an amorphous, slightly yellow imidazolidinyl compound) has a pH of about 8 in aqueous solution, a molecular weight of 530.57, a calculated empirical formula of $C_{25}H_{26}N_3NaO_5S.1.5H_2O$ and a melting point of 210° C.

EXAMPLE 9

2.5 ml. of 20% w/w aqueous solution of NaOH are added dropwise to 1.2 g. of isobutyraldehyde and the mixture is added to a stirred suspension of 6.5 g. amoxicillin trihydrate in 100 ml. $H_2O$. The resulting solution after filtration through a 0.45 μMillipore filter is frozen −60° C. and freeze dried.

The product, an amorphous, slightly yellow imidazolidinyl compound, has a pH of about 8.0 in aqueous solution, a molecular weight of 463.99, a calculated empirical formula of $C_{20}H_{24}N_3O_5NaS.1.25H_2O$ and a melting point of 192° C.

EXAMPLE 10

2.5 ml. of 20% w/w aqueous solution of NaOH are added dropwise to 2.0 g. of para-fluorobenzaldehyde and the mixture is added to a stirred suspension of 6.5 g. amoxicillin trihydrate in 100 ml. $H_2O$. The resulting solution after filtration through a 0.45 μMillipore filter is frozen at −60° C. and freeze dried.

The product, an amorphous slightly yellow material, has a structure which is not yet determined. It is probable that it is a mixture of imidazolidinyl compound and Schiff's base.

EXAMPLE 11

2.5 ml. of 20% w/w aqueous solution of NaOH are added dropwise to 1.9 g. of salicylaldehyde and the mixture is added to a stirred suspension of 6.5 g. amoxicillin trihydrate in 100 ml. water. The resulting solution, after filtration through a 0.45 μMillipore filter is frozen at −60° C. and freeze dried.

The product, an amorphous, slightly yellow material, is a Schiff's base. It has a pH of about 8.0 in aqueous solution, a molecular weight of 509.50, a calculated empirical formula of $C_{23}N_3SO_6Na.H_2O$ and a melting point of 205° C.

EXAMPLE 12

2.5 ml. of 20% w/w aqueous solution of NaOH are added dropwise to 2.4 ml. of caprylaldehyde and the mixture is added to a stirred suspension of 6.5 g. amoxicillin trihydrate in 100 ml. water. The resulting solution, after filtration through a 0.45 μMillipore filter is frozen at −60° C. and freeze dried.

9

The product, an amorphous, slightly yellow imidazolidinyl compound, has a pH of about 8 in aqueous solution, a molecular weight of 533.60, a calculated empirial formula of $C_{24}H_{32}N_{Na}O_5S \cdot 2H_2O$ and a melting point of 195° C.

EXAMPLE 13

2.5 ml. of a 20% w/w aqueous solution of NaOH was added dropwise to 2.1 ml. of hydrocinnammaldehyde. The mixture was added to a stirred suspension of 6.5 g. amoxicillin trihydrate in 100 ml. $H_2O$. The resulting clear solution after filtration through a 0.45 μ Millipore filter was frozen at −60° C. and freeze dried.

The product (an amorphous slightly yellow imidazolidinyl compound) has a molecular weight of 521.56 and a calculated emprical formula of $C_{25}H_{26}N_3O_5NaS \cdot H_2O$.

EXAMPLE 14

A solution for intramuscular injection is formed by dissolving 125 mg., 250 mg. or 500 mg. of active compound in respectively 1.0 cc., 0.9–1.9 cc. or 1.7 cc. sterile water injection USP.

EXAMPLE 15

Compositions for direct intravenous administration are made by dissolving 125 mg., 250 mg. or 500 mg. of active compound in 2 cc. or 5 cc. sterile water. 1000 mg. and 2000 mg. of active compound are dissolved in 7.5 cc. sterile water for show administration.

For intravenous drip administration, 1000 mg., 2000 mg. and 4000 mg. of active compound are dissolved in 7.5 cc. or 15 cc. sterile water and added to 250 cc. to 2000 cc. of intravenous solution.

We claim:
1. A compound represented by the formula

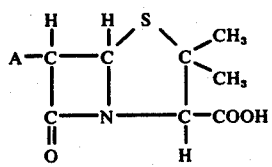

wherein A is

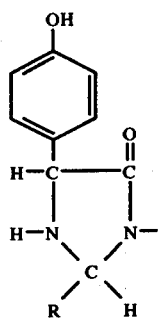

R is hydrogen, substituted or unsubstituted lower alkenyl or alkyl or 1 to 8 carbon atoms in the alkyl chain, phenyl,
and pharmaceutically acceptable salts with bases of said compounds.
2. The compound of claim 1 wherein R is methyl.
3. A stable aqueous injectable formulation containing as the active ingredient, the sodium salt of the compound of claim 2.
4. A stable aqueous injectable solution containing as the active ingredient the sodium salt of the compound of claim 2.
5. A compound represented by the formula

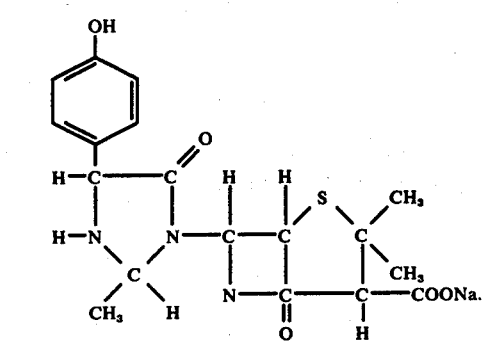

* * * * *